United States Patent [19]

Nagata et al.

[11] 4,342,685
[45] Aug. 3, 1982

[54] INVERSION OF THE 3 α-AMINO GROUP ATTACHED TO THE β-LACTAM RING

[75] Inventors: Wataru Nagata, Nishinomiya; Tsutomu Aoki, Sennan, both of Japan

[73] Assignee: Shionogi & Co., Ltd., Osaka, Japan

[21] Appl. No.: 136,073

[22] Filed: Mar. 28, 1980

[30] Foreign Application Priority Data

Apr. 3, 1979 [JP] Japan ................................. 54-40624

[51] Int. Cl.$^3$ ................. C07D 705/08; C07D 498/04; C07B 29/00
[52] U.S. Cl. .................................. 260/239 A; 544/90
[58] Field of Search ........................ 260/239 A, 245.4; 544/90

[56] References Cited

PUBLICATIONS

Vlietinck et al., Tet. Letters 1972, 285–287.
Firestone et al., J. Org. Chem. 39, 437–440 (1974).
Miyadera et al., Chem. Abs. 90, 186975h (1978).
Hiraoka et al., Chem. Abs. 90, 204118n (1978).

Primary Examiner—Mark L. Berch
Attorney, Agent, or Firm—Wenderoth, Lind & Ponack

[57] ABSTRACT

A process for preparing 3β-amino-4β-substituted-2-azetidinones, which comprises condensing a 3α-amino-4β-substituted-2-azetidinone with a trihalogenoacetaldehyde or the reactive derivative thereof to give a 3α-(2,2,2-trihalogenoethylidene)amino-4β-substituted-2-azetidinones, treating the latter with a base to give a 3-(2,2-dihalogenovinyl)imino-4β-substituted-2-azetidinone, reducing the latter with a metal hydride to give a 3β-(2-halogenovinyl)amino-4β-substituted-2-azetidinone, and hydrolyzing the latter to give the objective compound.

5 Claims, No Drawings

INVERSION OF THE 3 α-AMINO GROUP ATTACHED TO THE β-LACTAM RING

This invention relates to intermediates useful in the preparation of penicillins and cephalosporins and the preparation thereof. In another aspect, this invention relates to the inversion of the 3α-amino group attached to the β-lactam ring.

In the course of penicillin or cephalosporin total synthesis, 6α-aminopenicillanic acid derivatives or 7α-aminocephalosporanic acid derivatives are sometimes produced. In order to obtain useful penicillins or cephalosporins, it is usually necessary to convert the above 6α- or 7α-amino group into the useful 6β- or 7β-amino group. The inversion processes have been investigated and described in, for example, Japanese published patent application Nos. 49-125,389 and 50-106,993, Journal of the American Chemical Society, 99, 5505 (1977) and Tetrahedron Letters 1973, 4649. These well-known methods, however, provide low yield, and cannot be applied to compounds having an unstable group because of the strong reaction conditions. The present inventors have investigated in order to overcome the above defects of the well-known methods and have found the present novel inversion process of a 3α-amino group attached to the β-lactam ring.

The novel process of this invention can be represented as follows by the reaction scheme:

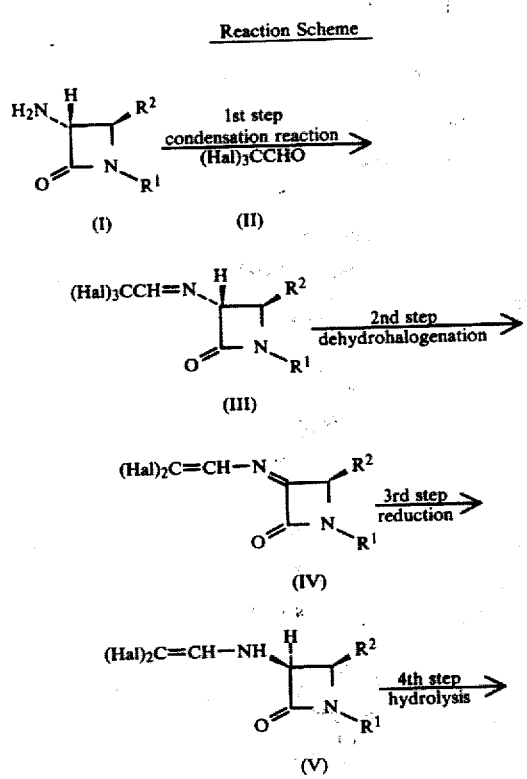

-continued
Reaction Scheme

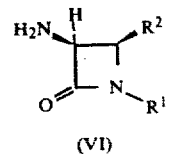

[wherein $R^1$ is a group of the formula:

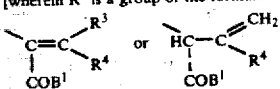

(wherein $R^3$ and $R^4$ are same or different lower alkyls; and $COB^1$ is carboxy or protected carboxy);
$R^2$ is alkenyloxy, alkynyloxy, alkanoyloxy, or alkylthio; or
$R^1$ and $R^2$ taken together represent a group of the formula:

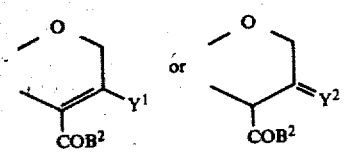

(wherein $Y^1$ is hydrogen, halogen, lower alkoxy, or lower alkyl which may be substituted by halogen, acyloxy, or heteroaromatic thio; $Y^2$ is alkylidene; and $COB^2$ is carboxy or protected carboxy);
Hal is halogen.]

In the above formulae, the dotted lines represent the α-configuration and the bold lines represent the β-configuration. The expressions "α" and "β" mean relative steric configuration. That is to say, in the formula (I), the 3-amino and the 4-$R^2$ groups are in the trans position and the 3-hydrogen and the 4-$R^2$ group are in the cis position. This invention also includes the inversion of the 3β-amino to 3α-amino.

The explanation of the each reaction process is as follows:

(First step)

This process is a condensation reaction and may be readily carried out by reacting a 3α-amino-4β-substituted-2-azetidinone [I] with an equimolar or excess amount of an aldehyde [II] or the reactive derivatives thereof in a suitable solvent under heating.

Representatives of the solvent are alcohols (e.g. methanol, ethanol, propanol, butanol, t-butanol, benzyl alcohol, ethylene glycol), ethers (e.g. diethyl ether, glyme, diglyme, tetrahydrofuran), hydrocarbons (e.g. benzene, toluene, xylene, methylene chloride), or the like or a mixture of two or more of them.

This reaction proceeds under the same condition as in the ordinal formation reaction of Schiff bases, but it is preferred to carry it out while removing the water produced during the reaction by means of a molecular sieve or the like.

(Second step)

This step is a dehydrohalogenation reaction, and may be carried out by reacting the Schiff Base (II) prepared in the 1st step with an equimolar or excess amount, preferably 1.1 to 2 equivalents, of a base in a suitable solvent.

The utilizable solvents are the same as the solvents exemplified in Example 1.

Representatives of bases are tertiary amines (e.g. triethylamine, ethyl diisopropylamine), alkoxide of alkali metals (e.g. lithium methoxide, potassium t-butoxide), pyridine, quinoline, or the like organic bases.

The reaction may be carried out under cooling, preferably at $-50°$ to $0°$ C., more preferably at $-40°$ to $-20°$ C. However, this reaction proceeds enough even at room temperature. The reaction is ordinarily complete within several tens of minutes, but the reaction runs often slower depending on varying reaction temperature, kinds of base, and other reaction conditions.

(Third step)

This process is a reduction of the imino group, and is carried out by reducing the imine compound (IV) prepared in the 2nd step with a reducing agent in a suitable solvent. The exemplified solvents in the 1st step may be also employed in this step. Among them, diethyl ether, tetrahydrofuran, and diglyme are more preferable.

Representatives of the said reducing agents are metal hydrides such as sodium borohydride, potassium borohydride, lithium aluminium hydride, sodium cyano borohydride, lithium aluminium trialkoxyhydride, aluminium diisobutylhydride and the like.

This reaction may be carried out at room temperature under stirring, but depending on the reaction species, this reaction is carried out under cooling, even at $-50°$ to $0°$ C.

(Fourth step)

This process is a hydrolysis reaction and may be carried out by treating an enamine compound (V) prepared in the 3rd step with an acid.

Representatives of the acid are inorganic acids such as hydrochloric acid, sulfuric acid, and the like and organic acids such as formic acid, acetic acid, oxalic acid, and the like.

This reaction is carried out in the presence of protic solvents such as water or an alcohol.

This reaction proceeds enough under ice-cooling or at room temperature, but if required, the reaction may be accelerated by warming.

The above 1st to 4th steps may be successively carried out in one vessel, or may be discontinuously carried out in order to isolate the desired intermediates. The intermediates (IV) and (V) are novel compounds.

This inversion process can be applied to the preparation of the strongly active antibacterial agents e.g. 1-oxacefalothin [J. A. C. S., 96; 24, 7582 (1974)] and 1-oxacefamandole [J. Med. Chem., 20, 551 (1977)]. In order to prepare these antibacterial agents, it is necessary to introduce stereospecifically the oxygen group in the β-configuration at the 4-position of the azetidinone ring. This operation was very difficult, however, the present inventors have found that this difficult problem might be solved by carrying out this operation after converting the 3β-acylamino of the starting materials into the 3α-acylamino (Japanese Unexamined Patent Publication No. 53-98951). The produced 3α-acylamino on the 2-azetidinone must be converted back to 3β-acylamino on the 2-azetidinones in a suitable step. This invention is applicable to this operation.

Compounds prepared by the process of this invention have the following general formula:

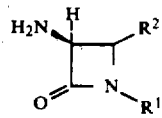

(wherein $R^1$ and $R^2$ each has the same meaning as mentioned above.)

In the above definition of each symbol, preferable Hal is chloro, bromo, or iodo. Lower alkyl as $R^3$ or $R^4$ may be $C_1$ to $C_3$ alkyl. Alkenyloxy and alkynyloxy as $R^2$ may be $C_2$ to $C_4$ alkenyloxy and alkynyloxy, respectively, and alkanoyloxy and alkylthio as $R^2$ may be $C_1$ to $C_4$ alkanoyloxy and alkylthio, respectively. Lower alkoxy and lower alkyl as $Y^1$ may be $C_1$ to $C_7$ alkoxy and lower alkyl, respectively. Alkylidene as $Y^2$ may be $C_1$ or $C_2$ alkylidene. $COB^1$ and $COB^2$ may be a conventional carboxylic ester group, for example, diphenylmethyl ester, 2,2,2-trichloroethyl ester, p-nitrobenzyl ester, p-methoxybenzyl ester, phthalidyl ester, acetoxymethyl ester, pivaloyloxymethyl ester, t-butyl ester, phenyl ester, indanyl ester, or the like group.

Representatives are compounds of which $R^1$ and $R^2$ are selected from the following groups:

| $R^1$ | $R^2$ |
|---|---|
| CH₃–C(CH₃)–COOCHPh₂ | –O–CH₂–C≡CH |
| CH₃–C(CH₃)–COOCHPh₂ | –SCH₃ |
| HC(=CH₂)–C(CH₃)–COOCHPh₂ | –SCH₃ |
| =C(–O–/)(COOCHPh₂)–CH₂–STetr | |
| =C(–O–/)(COOCHPh₂)–H | |
| =C(–O–/)(COOCHPh₂)–CH₃ | |
| =C(–O–/)(COOCHPh₂)–OCOCH₃ | |

| | -continued | |
|---|---|---|
| | R¹ | R² |
| | CH₃ (COOCHPh₂) | O-CH₂ with CH₂ (=CH₂) |
| | CH₃ (COOCHPh₂) | O-CH₂ with Cl |
| | CH₃ (COOCHPh₂) | O-CH₂ with OCH₃ |

Intermediates of this invention have the following general formulae:

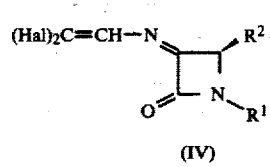

(IV)

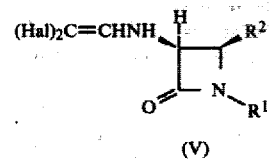

(V)

Representatives are compounds of which Hal, R¹ and R² are selected from the following groups:

| Hal | R¹ | R² |
|---|---|---|
| Cl | CH₃-C(CH₃)-COOCHPh₂ | O-CH₂-C≡CH |
| Cl | CH₃-C(CH₃)-COOCHPh₂ | —SCH₃ |
| Cl | CH₂=C(CH₃)-COOCHPh₂ | —SCH₃ |
| Cl | | O-CH₂ with STetr and COOCHPh₂ |
| Cl | | O-CH₂ with H and COOCHPh₂ |
| Cl | | O-CH₂ with CH₃ and COOCHPh₂ |

| Hal | R¹ | R² |
|---|---|---|
| Cl | | O-CH₂ with OCOCH₃ and COOCHPh₂ |
| Cl | | O-CH₂ with =CH₂ and COOCHPh₂ |
| Cl | | O-CH₂ with Cl and COOCHPh₂ |
| Cl | | O-CH₂ with OCH₃ and COOCHPh₂ |

The following examples are provided to further illustrate this invention.

Ph represents phenyl and Tetr represents 1-methyltetrazol-5-yl.

EXAMPLE 1-A

Diphenylmethyl 7α-(2,2,2-trichloroethylidene)amino-3-(1-methyltetrazol-5-yl)thiomethyl-1-oxadethia-3-cephem-4-carboxylate

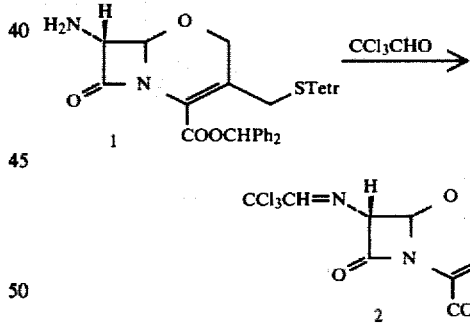

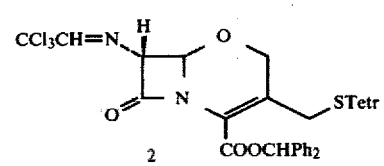

To a solution of 4.1 g of diphenylmethyl 7α-amino-3-(1-methyltetrazol-5-yl)thiomethyl-1-oxadethia-3-cephem-4-carboxylate 1 in 130 ml of benzene are added 6.85 ml of trichloroacetaldehyde and 13.5 g of 3 A Molecular Sieves, and the mixture is stirred for 2.5 hours under nitrogen atmosphere and filtered. The filtrate is concentrated under reduced pressure and the residue is chromatographed on prepacked silica gel column [Merck AG; size C/benzene-ethyl acetate (1:1)] to give 2.566 g of the title compound 2 as yellow crystals in 50% yield. mp. 146°–149° C.

IR: $\nu_{max}^{CHCl_3}$ 1788, 1723 cm⁻¹.

NMR: $\delta^{CDCl_3}$ 3.85(s, 3H), 4.33(s,2H), 4.75(s,2H), 4.88(d,J=2 Hz,1H), 5.20(s,1H), 6.97(s,1H), 7.32–7.80(m,10H), 8.15(d,J=2 Hz,1H).

EXAMPLE 1-B

Diphenylmethyl 7-(2,2-dichlorovinyl)imino-3-(1-methyltetrazol-5-yl)thiomethyl-1-oxadethia-3-cephem-4-carboxylate

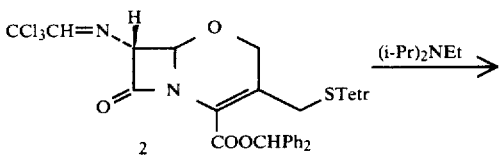

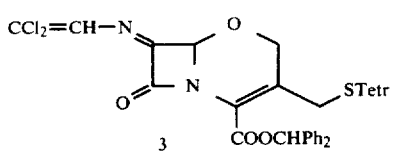

To a solution of 2.363 g of diphenylmethyl 7α-(2,2,2-trichloroethylidene)amino-3-(1-methyltetrazol-5-yl)thiomethyl-1-oxadethia-3-cephem-4-carboxylate 2 in 25 ml of dichloromethane is added 772 μl of ethyl-diisopropylamine at −40° C. under nitrogen atmosphere, and the mixture is stirred for 20 minutes, poured into ice-cooled 2 N hydrochloric acid, and extracted with dichloromethane. The extract is washed with aqueous sodium hydrogencarbonate and water, dried, and evaporated. The residue is crystallized from ether to give 2.110 g of the title compound 3 in 95% yield.

mp. 186°–189° C.

NMR: $\delta^{CDCl_3}$ 3.83(s,3H), 4.33(s,2H), 4.73(s,2H), 5.47–5.50(2s,1H), 6.97(s,1H), 7.13–7.83(m,10H), 8.03(s,1H).

EXAMPLE 1-C

Diphenylmethyl 7β-(2,2-dichlorovinyl)amino-3-(1-methyltetrazol-5-yl)thiomethyl-1-oxadethia-3-cephem-4-carboxylate

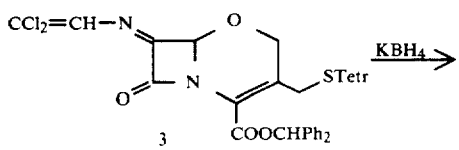

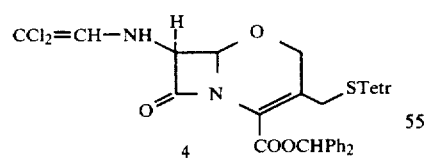

To a solution of 440 mg of diphenylmethyl 7-(2,2-dichlorovinyl)imino-3-(1-methyltetrazol-5-yl)thiomethyl-1-oxadethia-3-cephem-4-carboxylate 3 in 8 ml of tetrahydrofuran is added a solution of 48 mg of potassium borohydride in 12 ml of 50% tetrahydrofuran, and the mixture is vigorously stirred for 3 minutes and treated in a conventional manner to give the title compound 4.

NMR: $\delta_{ppm}^{CDCl_3}$ 2.30(s,3H), 4.28(s,2H), 4.50(d,J=3 Hz,1H), 4.68(s,2H), 5.03(d,J=3 Hz,1H), 5.31(s,1H), 6.93(s,1H), 7.2–7.7(m,10H).

EXAMPLE 1-D

Diphenylmethyl 7β-amino-3-(1-methyltetrazol-5-yl)thiomethyl-1-oxadethia-3-cephem-4-carboxylate

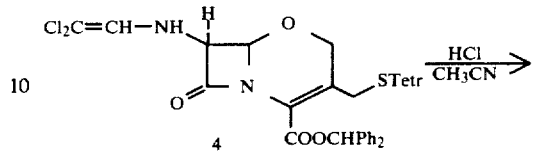

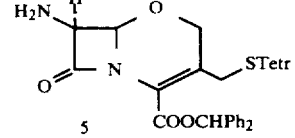

To the resulting solution containing diphenylmethyl 7β-(2,2-dichlorovinyl)amino-3-(1-methyltetrazol-5-yl)thiomethyl-1-oxadethia-3-cephem-4-carboxylate 4 in Example 1-C are added 12 ml of cooled 2 N hydrochloric acid and 6 ml of acetonitrile, and the mixture is stirred for 2.5 hours under ice-cooling, poured into an aqueous sodium hydrogencarbonate solution and extracted with dichloromethane. The extract is washed with water, dried, and evaporated. The residue is triturated with ether and the resulting powder is chromatographed on a prepacked silica gel column (Merck AG; size B/ethyl acetate) and crystallized from ethyl acetate-ether to give 154 mg of the title compound 5.

mp. 151°–154° C.

NMR: $\delta_{ppm}^{CDCl_3}$ 1.87(s,2H), 3.77(s,3H), 4.25(s,2H), 4.47(d,J=4 Hz,1H), 4.63(s,2H), 4.95(d,J=4 Hz,1H), 6.90(s,1H), 7.13–7.67(m,10H).

EXAMPLE 2

(Continuous operation)

Diphenylmethyl 7β-amino-3-(1-methyltetrazol-5-yl)thiomethyl-1-oxadethia-3-cephem-4-carboxylate

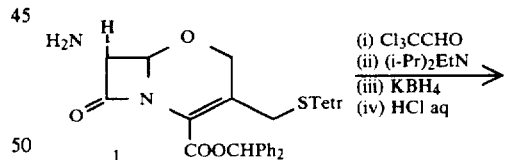

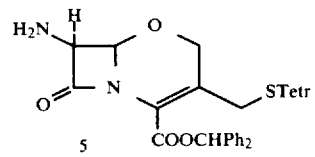

To a solution of 205 mg of diphenylmethyl 7α-amino-3-(1-methyltetrazol-5-yl)thiomethyl-1-oxadethia-3-cephem-4-carboxylate 1 and 0.343 ml of trichloroacetaldehyde in 7 ml of anhydrous benzene is added 680 mg of 3 A Molecular Sieves and the mixture is refluxed for 2.5 hours and filtered. The filtrate is concentrated under reduced pressure. The residue is dissolved in 2 ml of tetrahydrofuran and mixed with 76.3 μl of ethyl-diisopropylamine at −40° C. under nitrogen atmosphere. After 20 minutes, the reaction mixture is warmed to 0°

C. and mixed with 3 ml of a solution of 51 mg of potassium borohydride in 50% tetrahydrofuran and after 3 minutes, mixed with 3 ml of 2 N hydrochloric acid and 1.5 ml of acetonitrile. The mixture is stirred for 2 hours under ice-cooling, poured into an aqueous sodium hydrogencarbonate solution, and extracted with dichloromethane. The extract is washed with water, dried, and evaporated. The residue is crystallized from ethyl acetate to give 90 mg of the title compound 5 in 46.34% yield.

mp. 138°–146° C.

Examples 3 to 8 - A
The following compounds may be prepared in the same manner as Example 1-A.

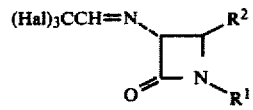

| Ex. No. | R¹ | R² | Hal | Yield (%) | mp (°C.) | IR:$\nu_{max}^{CHCl_3}$ cm$^{-1}$ | NMR:$\delta^{CDCl_3}$ |
|---|---|---|---|---|---|---|---|
| 3 | — | (structure with O, H, COOCHPh₂) | Cl | 41.5 | — | — | 4.50(d,J = 3Hz,2H),4.82(s,1H), 5.05(s,1H),6.47(t,J = 3Hz,1H), 6.95(s,1H),7.2–7.6(m,10H), 8.07(s,1H) |
| 4 | — | (structure with O, OCOCH₃, COOCHPh₂) | " | 53 | — | — | 2.00(s,3H),4.50(s,2H),4.82 (m,1H),4.88 + 5.18(Abq,2H), 5.10(s,1H),6.92(s,1H),7.2– 7.7(m,10H),8.09(d,1H) |
| 5 | — | (structure with O, CH₂, COOCHPh₂) | " | — | — | — | 4.30(s,2H),4.76(s),4.80(s, 1H),5.20(s,1H),5.28(s,1H), 5.36(s,1H),5.41(s,1H),6.91 (s,1H),7.2–7.6(m,10H),8.00 (s),8.07(s,1H) |
| 6 | (trans) C(CH₃)₂COOCHPh₂ | O—CH₂—C≡CH | " | — | — | — | 2.07(s,3H),2.28(s,4H),3.98 (brs,1H),4.10(d,J = 3Hz,2H), 5.51(brs,1H),7.08(s,1H),7.2– 7.7(m,10H),8.16(d,J = 2Hz,1H) |
| 7 | (cis) C(CH₃)₂COOCHPh₂ | —SCH₃ | " | 46 | — | — | 1.93(s,3H),2.06(s,3H),2.28 (s,3H),5.05–5.55(m,2H),7.00 (s,1H),7.2–7.5(m,10H),8.1 (d,J = 2Hz,1H) |
| 8 | — | (structure with O, CH₃, COOCHPh₂) | " | 68 | 140–142 | 1783,1723, 1660 | 2.16(s,3H),4.17(s,1H),4.40 (s,2H),4.83(d,J = 2Hz,1H), 5.15(s,1H),7–7.8(m,10H), 8.13(d,J = 2Hz,1H) |

Examples 3 to 8 - B
The following compounds may be prepared in the same manner as Example 1-B.

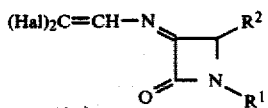

| Ex. No. | R¹ | R² | Hal | Yield (%) | mp (°C.) | IR:$\nu_{max}^{CHCl_3}$ cm$^{-1}$ | NMR:$\delta^{CDCl_3}$ |
|---|---|---|---|---|---|---|---|

-continued

| Ex. | R¹ | R² | | | IR | NMR |
|---|---|---|---|---|---|---|
| 3 | (structure: methoxy vinyl with COOCHPh₂, H) | Cl | — | — | — | — |
| 4 | (structure: methoxy vinyl with COOCHPh₂, CH₂OCOCH₃) | " | — | — | — | 2.00(s,3H),4.50(s,2H),4.33 + 5.23(ABq,2H),5.37(s,1H),6.90 (s,1H),7.2-7.7(m,10H),7.97 (s,1H) |
| 5 | (structure: methoxy with COOCHPh₂, =CH₂) | " | — | — | — | 4.31(s,2H),5.30(s,2H),5.40(s, 1H),5.71(s,1H),5.76(s,1H), 6.87(s,1H),7.1-7.5(m,10H), 7.86(s,1H) |
| 6 (trans) | (CH₃)₂C=C(COOCHPh₂)- | —OCH₂C≡CH | " | — | — | 3300,1780, 1725. | 2.03(s,3H),2.31(s,3H),4.18(d, 2H),5.83(s,1H),7.00(s,1H),7.1- 7.6(m,10H),8.03(s,1H) |
| 7 (cis) | (CH₃)₂C=C(COOCHPh₂)- | —SCH₃ | " | — | — | — | 1.92(s,3H),2.0(s,3H),2.28(s, 3H),5.55(s,1H),6.97(s,1H),7.2- 7.6(m,10H),8.03(s,1H) |
| 8 | (structure: methoxy with COOCHPh₂, CH₃) | | " | — | — | 1780,1725 (CHCl₃) | 1.93(s,3H),4.20(s,2H),5.27(s, 1H),6.97(s,1H),7.1-7.7(m, 10H),8.03(s,1H) |

Examples 3 to 8 - C to D
The following compounds may be prepared in the same manner as Examples 1-C and D.

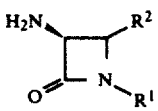

| Ex. No. | R¹ | R² | Yield (%) | mp (°C.) | IR:$\nu_{max}^{Nujol}$ cm⁻¹ | NMR:$\delta^{CDCl_3}$ |
|---|---|---|---|---|---|---|
| 3 | | (structure: methoxy vinyl with COOCHPh₂, H) | 50 | — | 3530,3400,1785, 1725,1640 | — |
| 4 | | (structure: methoxy vinyl with COOCHPh₂, CH₂OCOCH₃) (hydrochloride) | — | — | 3400,1795,1730 | 2.01(s,3H),3.92(brs,3H),4.60 (brs,2H),4.90(d,J = 4Hz,1H), 5.10(d,J = 4Hz,1H),5.20(d,J = 4Hz,1H),6.90(s,1H),7.2-7.6(m, 10H) |
| 5 | | (structure: methoxy with COOCHPh₂, =CH₂) | — | — | 3350,1775,1745 | 1.9(br,2H),4.30(s,2H),5.1- 5.3(m,2H),5.10(s,1H),5.25(s, 1H),5.30(s,1H),6.83(s,1H), 7.15-7.6(m,10H) |
| 6 | (CH₃)₂C=C(COOCHPh₂)- | —OCH₂C≡CH | — | — | 3410,3320,2115, 1767,1720(CHCl₃) | 1.25(brs,3H),2.03(s,3H),2.26 (s,3H),4.16(brd,J = 3Hz,3H), 5.33(d,J = 3Hz,1H),6.97(s,1H), 7.15-7.5(m,10H) |

| 7 | CH₃ attached with CH₃ and COOCHPh₂ | —SCH₃ | — | — | — | 1.8(brs,2H),1.9(s,3H),2.01(s, 3H),2.25(s,3H),4.45(d,J = 5Hz, 2H),4.96(d,J = 5Hz,2H),7.0(s, 1H),7.2–7.5(m,10H) |
| 8 | structure with O, CH₃, COOCHPh₂ | | — | — | — | 1.77(brs,2H),2.0(s,3H),4.3(s, 2H),4.46(d,J = 4Hz,1H),4.97(d, J = 4Hz,1H),6.9(s,1H),7.2–7.6 (m,10H) |

Examples 9 to 10
The following compounds may be prepared in the same manner as Example 2.

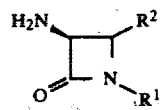

| Ex. No. | R¹ | R² | Yield (%) | mp (°C.) | IR:$\nu_{max}^{Nujol}$ cm$^{-1}$ | NMR:$\delta^{CDCl_3}$ |
|---|---|---|---|---|---|---|
| 9 | structure with O, Cl, COOCHPh₂ | | 55.3 | — | 1785,1720, 1710 | 2.07(brs,2H),4.40(s,2H), 4.45(d,J = 4Hz,1H),4.98(d, J = 4Hz,1H9,6.97(s,1H),7.2– 7.6(m,10H) |
| 10 | structure with O, OCH₃, COOCHPh₂ | | 34 | — | 3520,3400, 1785,1725, 1630 | 1.75(brs,2H),3.77(s,3H), 4.48(d,J = 4Hz,1H),4.52(s, 2H),4.98(d,J = 4Hz,1H),6.98 (s,1H),7.2–7.6(m,10H) |

EXAMPLE 11

Diphenylmethyl 7β-(α-chloroacetamido)-3-chloromethyl-1-oxadethia-3-cephem-4-carboxylate

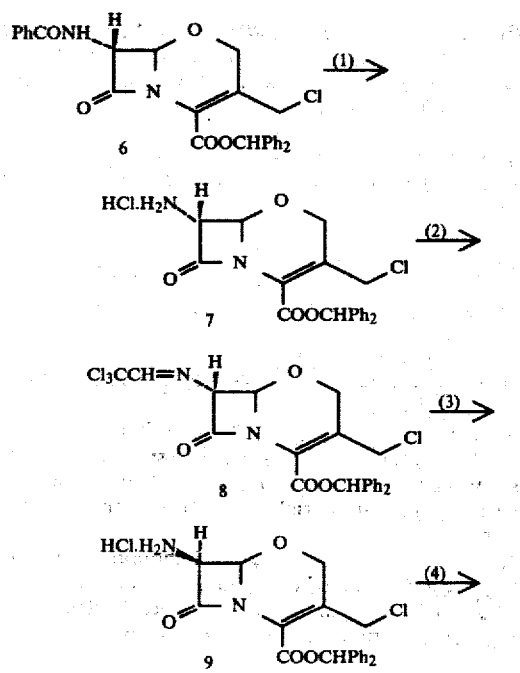

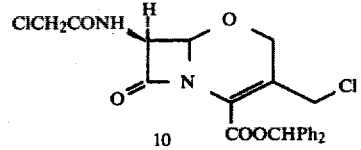

(1) To a solution of 450 mg (0.9 mmole) of diphenylmethyl 7α-benzoylamino-3-chloromethyl-1-oxadethia-3-cephem-4-carboxylate 6 in 9 ml of methylene chloride are added 375 mg (1.8 mmoles) of phosphorus pentachloride, 146 μl (1.8 mmoles) of pyridine and 1 μl of dimethylformamide in turn, and the mixture is stirred for 2.5 hours under ice-cooling. Isobutanol (9 ml) is added thereto, and the mixture is allowed to stand at 3° C. overnight and evaporated under reduced pressure. The residue is treated with ether to give diphenylmethyl 7α-amino-3-chloromethyl-1-oxadethia-3-cephem-4-carboxylate hydrochloride as crude product.

(2) To a solution of the above crude product in 6 ml of dichloromethane is added 97.5 μl (0.99 mmole) of trichloroacetaldehyde. The mixture is refluxed for 4.5 hours, while the additional 97.5 μl of trichloroacetaldehyde is added thereto over 1 hour period. The reaction mixture is concentrated under reduced pressure and the residue is chromatographed on a column of silica gel and eluted with benzene to give 281 mg of diphenylmethyl 7α-(2,2,2-trichloroethylidene)amino-3-chloromethyl-1-oxadethia-3-cephem-4-carboxylate as yellow foamy materials. (yield from Compound 6:63%).

IR: $\nu_{max}^{CHCl_3}$ 1787, 1726 cm$^{-1}$.
NMR: $\delta_{ppm}^{CHCl_3}$ 4.53(s,2H), 4.62(s,2H), 4.83–4.97(m,1H), 5.20(s,1H), 6.98(s,1H), 7.17–7.77(m,10H), 8.13(d,J=2 Hz,1H).

(3) To a solution of 105 mg (0.2 mmole) of diphenylmethyl 7α-(2,2,2-trichloroethylidene)amino-3-chloromethyl-1-oxadethia-3-cephem-4-carboxylate 8 in 2 ml of tetrahydrofuran is added 37.4 μl (0.21 mmole) of ethyl diisopropylamine at −40° C., and the mixture is stirred at the same temperature for 20 minutes. A solution of 12 mg (0.222 mmole) of potassium borohydride in 0.5 ml of tetrahydrofuran and 0.5 ml of water is added thereto, and the mixture is reacted for 5 minutes under ice-cooling and mixed with 2 ml of 2 N hydrochloric acid, 1 ml of acetonitrile and 1 ml of tetrahydrofuran. After 1.5 hours, the reaction mixture is concentrated under reduced pressure and extracted with dichloromethane. The extract is washed with brine, dried and evaporated to give 60 mg of diphenylmethyl 7β-amino-3-chloromethyl-1-oxadethia-3-cephem-4-carboxylate hydrochloride 9 as crude product.

(4) To a solution of 60 mg of diphenylmethyl 7β-amino-3-chloromethyl-1-oxadethia-3-cephem-4-carboxylate hydrochloride 9 in 2 ml of methylene chloride are added 20.6 μl (0.276 mmole) and 41.8 μl of pyridine. After 30 minutes, the reaction mixture is poured into 2 N hydrochloric acid and extracted with methylene chloride. The extract is dried and concentrated. The residue is chromatographed on a prepacked silica gel column size A (Merck) and eluted with benzene and ethyl acetate (2:1) to give 44 mg of diphenylmethyl 7β-(α-chloroacetamido)-3-chloromethyl-1-oxadethia-3-cephem-4-carboxylate 10.

IR: $\nu_{max}^{CHCl_3}$ 3405, 1796, 1724, 1683 cm$^{-1}$.
NMR: $\delta^{CDCl_3}$ 4.13(s,2H), 4.58(s,4H), 5.10(d,J=4 Hz,1H), 5.70(dd,J=10.4 Hz,1H), 6.98(s,1H), 7.07–7.70(m,10H).

We claim:
1. A process for the preparation of a 3β-amino-4β-substituted-2-azetidinone of the formula

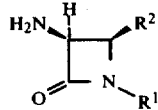

wherein R$^1$ is a group of the formula

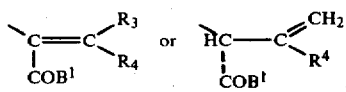

in which R$^3$ and R$^4$ are the same or different C$_1$ to C$_3$ alkyl and COB$^1$ is carboxy or a conventional carboxylic ester group, and R$^2$ is C$_2$ to C$_4$ alkenyloxy, C$_2$ to C$_4$ alkynyloxy, C$_1$ to C$_4$ alkanoyloxy or C$_1$ to C$_4$ alkylthio, or R$^1$ and R$^2$ taken together represent a group of the formula

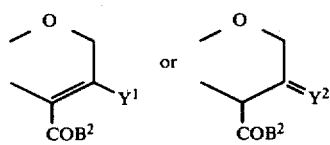

wherein Y$^1$ is hydrogen, halogen, C$_1$ to C$_7$ alkoxy or C$_1$ to C$_7$ alkyl which is unsubstituted or monosubstituted by halogen, acetoxy or 1-methyl-tetrazol-5-yl-thio, Y$^2$ is C$_1$ to C$_2$ alkylidene, and COB$^2$ is carboxy or a conventional carboxylic ester group, which comprises condensing a 3α-amino-4β-substituted-2-azetidinone of the formula

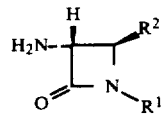

wherein R$^1$ and R$^2$ are as previously defined, with a trihalogenoacetaldehyde of the formula

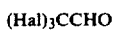

wherein Hal is chloro, bromo or iodo, to form a 3α-(2,2,2-trihalogenoethylidene)amino-4β-substituted-2-azetidinone of the formula

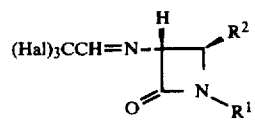

treating the thus formed compound with a base to give a 3-(2,2-dihalogenovinyl)imino-4β-substituted-2-azetidinone of the formula

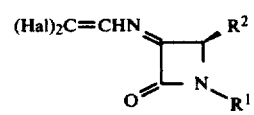

reducing the latter compound with a metal hydride to give a 3β-(2-halogenovinyl)amino-4β-substituted-2-azetidinone of the formula

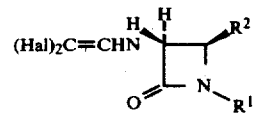

and hydrolyzing the latter compound with aqueous acid to yield the 3β-amino-4β-substituted-2-azetidinone compound, wherein the conventional carboxylic ester group is diphenyl methyl ester, 2,2,2-trichloroethyl ester, p-nitrobenzyl ester, p-methoxybenzyl ester, phthalidyl ester, acetoxymethyl ester, pivaloyloxymethyl ester, t-butyl ester, phenyl ester, or indanyl ester.

2. A process claimed in claim 1, wherein the base is a tertiary amine selected from the group of triethylamine and ethyl diisopropylamine, an alkoxide of alkali metal selected from the group of lithium methoxide and potassium t-butoxide or an organic base selected from the group of pyridine and quinoline.

3. A process claimed in claim 1, wherein the base is diisopropylamine.

4. A process claimed in claim 1, wherein the metal hydride is sodium borohydride, potassium borohydride, lithium aluminum hydride, cyano sodium borohydride, lithium aluminum trialkoxyhydride or aluminum diisobutylhydride.

5. A process claimed in claim 1, wherein the acid is an inorganic acid selected from the group of hydrochloric acid and sulfuric acid or an organic acid selected from the group of formic acid and acetic acid.

* * * * *